United States Patent
Guerret et al.

(10) Patent No.: US 10,227,321 B2
(45) Date of Patent: Mar. 12, 2019

(54) SOOTHING PRO-PHEROMONAL COMPOSITION FOR MAMMALS

(71) Applicant: Melchior Material And Life Science France, Lacq (FR)

(72) Inventors: Olivier Guerret, Pern (FR); Loic Guilonneau, Pau (FR); Samuel Dufour, Orthez (FR)

(73) Assignee: Melchior Material And Life Science France (FR)

( * ) Notice: Subject to any disclaimer, the term of this patent is extended or adjusted under 35 U.S.C. 154(b) by 0 days.

(21) Appl. No.: 15/539,372

(22) PCT Filed: Dec. 24, 2015

(86) PCT No.: PCT/EP2015/081241
§ 371 (c)(1),
(2) Date: Jun. 23, 2017

(87) PCT Pub. No.: WO2016/102706
PCT Pub. Date: Jun. 30, 2016

(65) Prior Publication Data
US 2017/0369465 A1  Dec. 28, 2017

(30) Foreign Application Priority Data
Dec. 26, 2014 (FR) .................... 14 63359

(51) Int. Cl.
*C07D 317/22* (2006.01)
*A61K 9/00* (2006.01)
*A61K 31/19* (2006.01)
*A61K 31/341* (2006.01)
*A61K 31/215* (2006.01)
*A61K 47/06* (2006.01)

(52) U.S. Cl.
CPC ............ *C07D 317/22* (2013.01); *A61K 9/007* (2013.01); *A61K 31/19* (2013.01); *A61K 31/341* (2013.01); *A61K 31/215* (2013.01); *A61K 47/06* (2013.01)

(58) Field of Classification Search
CPC ..................................... C07D 317/22
USPC .......................................... 514/693
See application file for complete search history.

(56) References Cited

U.S. PATENT DOCUMENTS 3,883,558 A * 5/1975 Lamparsky ......... A23L 27/2052
549/454
6,077,867 A   6/2000 Pageat 6,576,252 B2   6/2003 Schwartz et al.
8,741,965 B2   6/2014 Nouvel et al.
2013/0210927 A1   8/2013 Nouvel et al.

FOREIGN PATENT DOCUMENTS

| EP | 0724832 A1 | 8/1996 |
| WO | 2009134958 A2 | 11/2009 |
| WO | 2009144321 A1 | 12/2009 |
| WO | 2011084795 A1 | 7/2011 |

OTHER PUBLICATIONS

Charra et al., "Brain processing of the mammary pheromone in newborn rabbits", Behavioural Brain Research, vol. 226, Issue 1, Jan. 2012, pp. 179-188.
Coureaud, "Newborn rabbit responsiveness to the mammary pheromone is concentration-dependent", Chemical Senses, vol. 29, Issue 4, May 2004, pp. 341-350.
Dantzer, "New aspects of the use of tranquillizers in animal husbandry, with particular reference to pigs", Veterinary Research Communications, Dec. 1977, vol. 1, Issue 1, pp. 161-169.
International Search Report for PCT/EP2015/081241 dated Mar. 18, 2016.
McGlone, "Olfactory signals that modulate pig aggressive and submissive behavior", Department of Animal Science, Texas Tech University, Lubbock, TX 79409-2141, USA, Social stress in domestic animals, 1990, pp. 86-109.
Schaal, "Chapter Four—Mammary Odor Cues and Pheromones: Mammalian Infant-Directed Communication about Maternal State, Mammae, and Milk", Vitamins & Hormones, vol. 83, Jan. 2010, pp. 83-136.

* cited by examiner

*Primary Examiner* — Nizal S Chandrakumar
(74) *Attorney, Agent, or Firm* — Lerner, David, Littenberg, Krumholz & Mentlik, LLP

(57) ABSTRACT

The invention relates to a compound of general formula (I) (in configuration Z or E) and to pro-pheromonal compositions and formulations comprising said compound, in addition to the uses thereof for soothing purposes for non-human mammals such as sheep, pigs, sheep, cattle, felines, equines and canines.

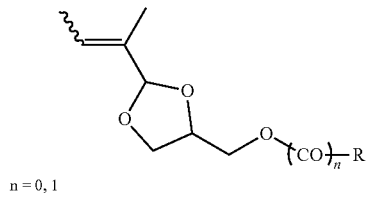

n = 0, 1

12 Claims, No Drawings

SOOTHING PRO-PHEROMONAL COMPOSITION FOR MAMMALS

CROSS REFERENCE TO RELATED APPLICATIONS

The present application is a national phase entry under 35 U.S.C. § 371 of International Application No. PCT/EP2015/081241, filed Dec. 24, 2015, published in French, which claims priority from French Patent Application No. 1463359, filed Dec. 26, 2014, all of which are incorporated herein by reference.

SUMMARY

The present invention relates to a compound of the general formula (1) (in a Z or E configuration) and to pro-pheromonal compositions and formulations comprising said compound. The advantage of such compositions is to allow controlled and prolonged release and diffusion of 2-methyl-2-butenal and fatty acid(s) added to the compositions and formulations.

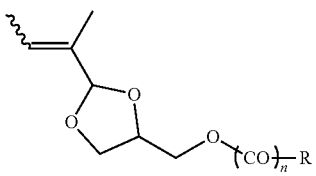

n = 0, 1

CONTEXT

In his interaction with domestic animals, whether pets or livestock, it is in man's interest that the latter have a calm and pacified behavior. In the particular case of pigs, these animals are known to develop aggressive behavior in normal situations, and especially in stressful situations. This aggressive behavior is expressed notably as fighting between pigs or even piglets and as attempts to escape (McGlone J. J., J. Animal Sci., 1990, Volume 68, 86-97). In order to reduce this behavior and to enable better fattening of farmed pigs, numerous neuroleptic treatments have been tested and have shown their efficacy (see for example the review by Dantzer R, Vet. Comm., 1977, Volume 1, 161-177). But the long-term indirect effects on individuals who consume the meat of pigs thus treated have remained little-known and have caused enough concern that other solutions are envisaged. Consequently, for many years, various solutions have been proposed for the various types of domestic animals, notably the use of compositions containing pheromones.

In order to better interact with the animal, compositions based on pheromones produced by the species in question were first developed. For example, to calm dogs, a composition containing a soothing artificial pheromone copying the natural pheromone produced by brood bitches to reassure their pups has shown its efficacy (patent WO2009134958). Likewise, to solve the problem of territory marking by cats (urine, scratches, etc.), a composition combining a set of fatty acids present in cats' natural facial pheromones and soothing or attractive plant substances (extract of valerian) was developed (EP0724832). Other anti-stress compositions also proved their efficacy, such as compositions based on squalene, on linoleic acid and on docosanol for dogs (WO2011084795), compositions based on a specific ratio of linoleic and linolenic acid (58%/13%) with addition of a flavonoid (ginger-type) and optionally other additions (hop and tryptophan known for its sedative effect) (U.S. Pat. No. 6,576,252), or compositions comprising at least three fatty acids present in the mammary glands of females, including palmitic acid, capric acid, lauric acid, oleic acid, myristic acid and linoleic acid. These last compositions proved effective for various mammals, in particular piglets (U.S. Pat. No. 6,077,867).

This first series of work was supplemented by another approach consisting in identifying substances derived from the mammary glands of species other than the one to be soothed (for example rabbits) and studying how it affects the behavior of another species. Thus, it was shown that the rabbit maternal pheromone, 2-methyl-2-butenal (see work by the Coureaud team cited below or the review by B. Schaal, Vitamins and Hormones, Volume 83, 2010, Ch. IV, p. 83), which is emitted to guide blind young rabbits toward the doe's teats until they are weaned, has an effect on the heartbeat and the behavior of dogs (patent US20140603). However, these various studies show that the efficacy period of rabbit's milk is short (less than 3 hours) and that the mixtures containing 2-methyl-2-butenal have a much-reduced efficacy over time when they are diffused by thermal diffusers (patent US20140603).

It is not surprising that such problems exist since the boiling point of 2-methyl-2-butenal is 116° C. at atmospheric pressure whereas fatty acids or derivatives thereof have boiling points above 200° C. under low atmospheric pressures (for example, linoleic acid has a boiling point of 230° C. under 16 mmHg). However, if 2-methyl-2-butenal is effective in very small amounts (between $10^{-5}$ and $10^{-9}$ g/L according to the publications by Coureaud: Coureaud G. et al., Chem. Sens. Volume 29, 2004, 341-350), fatty acids are generally used at higher concentrations of roughly $10^{-1}$ to $10^{-2}$ g/L, corresponding to daily rates above 10 mg/day and up to 200 mg/day (patent WO2009144321). For such orders of magnitude to be respected, the relative volatilities of the compounds have to be the opposite of what they are.

INVENTION

The invention thus relates to a formulation for releasing 2-methyl-2-butenal slowly and at doses below $10^{-7}$ g/day, whereas fatty acids are released at daily rates above $10^{-2}$ to $10^{-3}$ g/day. To achieve this goal, the Applicant deserves credit for synthesizing a novel compound of the general formula (1). During the diffusion of a composition or formulation containing one or more fatty acids associated with said compound (1), 2-methyl-2-butenal will be produced "in situ" by decomposition of the compound (1) and thus the simultaneous release thereof with that of the fatty acids will be better controlled.

To that end, the present invention concerns, in a first embodiment, a compound of the general formula (1):

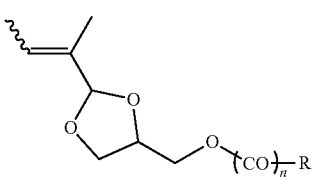

n = 0, 1 wherein n is equal to 0 or 1 and R represents a saturated or unsaturated linear alkyl group having 2 to 30 carbon atoms.

In a second embodiment of the present invention, the compound of the general formula (1) is characterized in that n=0 and R is a saturated or unsaturated linear alkyl group having 9 to 30 carbon atoms, more particularly 12 to 30 carbon atoms.

In a third embodiment of the invention, the compound (1) is characterized in that n=1 and R is a saturated or unsaturated linear alkyl group having 2 to 30 carbon atoms, more particularly 8 to 22 carbon atoms.

In an embodiment of the invention, the group R is unsaturated, in particular monounsaturated. R can also be diunsaturated.

In a preferred embodiment, the compound (1) is in Z form.

According to a fourth embodiment, the present invention concerns a compound (1) according to one of embodiments 1 to 3 for use as a veterinary medicinal product for treating anxiety, stress or aggressiveness in a non-human mammal.

According to a fifth embodiment, the present invention concerns a compound (1) according to the fourth embodiment, characterized in that the non-human mammal is selected from the group consisting of pigs, sheep, horses, cattle, cats and dogs.

In a particular embodiment, the non-human mammal is a pig.

In a particular embodiment, the non-human mammal is a dog.

In a particular embodiment, the non-human mammal is a cat.

In a particular embodiment, the non-human mammal is a cow.

In a sixth embodiment, the invention concerns a veterinary composition comprising a compound (1) according to one of embodiments 1 to 3 and at least one fatty acid or a derivative thereof.

The present invention, in a seventh embodiment, concerns a composition according to the sixth embodiment, characterized in that the fatty acid comprises 6 to 30 carbon atoms or a derivative of such a fatty acid selected from esters, thioesters or amides. Particularly, the fatty acid comprises 10 to 22 carbon atoms.

According to an eighth embodiment, the present invention is directed at a composition according to the sixth or seventh embodiment, characterized in that the fatty acid is selected from the group consisting of lauric acid, linoleic acid, linolenic acid, palmitic acid, pentadecanoic acid, capric acid, oleic acid, myristic acid, palmitoleic acid, azelaic acid, pimelic acid and mixtures thereof.

In a ninth embodiment, the invention concerns a composition according to one of embodiments 6 to 8, characterized in that the amount of the compound (1) is between 0.1% and 5% by weight of the composition.

According to a tenth embodiment, the present invention concerns a composition according to one of embodiments 7 to 9, characterized in that the amount of fatty acid or fatty acid derivative is between 95% and 99.9% by weight of the composition.

The present invention also concerns, in an eleventh embodiment, a formulation comprising a composition according to one of embodiments 7 to 10 and a solvent.

It is also a twelfth embodiment of the present invention to provide a formulation according to the eleventh embodiment, characterized in that the solvent is selected from the group consisting of water, alcohols, glycols, polyglycols, paraffin and mixtures thereof.

In a thirteenth embodiment, the invention is directed at a formulation according to the twelfth embodiment, characterized in that the solvent is selected from the group consisting of water, ethanol, isopropanol, paraffin, dipropylene glycol methyl ether, propylene glycol propyl ether, tripropylene glycol methyl ether and mixtures thereof.

In a fourteenth embodiment, the present invention is directed at a composition according to one of embodiments 6 to 13, for use as a veterinary medicinal product for treating anxiety, stress or aggressiveness in a non-human mammal.

It is a fifteenth embodiment of the present invention to provide a composition according to the fourteenth embodiment characterized in that the non-human mammal is selected from the group consisting of pigs, sheep, horses, cattle, cats and dogs.

In a particular embodiment, the non-human mammal is a pig.

In a particular embodiment, the non-human mammal is a dog.

In a particular embodiment, the non-human mammal is a cat.

In a particular embodiment, the non-human mammal is a cow.

The present invention also concerns, in a sixteenth embodiment, a formulation according to one of embodiments 11 to 13 for use as a veterinary medicinal product for treating anxiety, stress or aggressiveness in a non-human mammal.

In a seventeenth embodiment, the present invention is directed at a formulation according to the sixteenth embodiment, characterized in that the non-human mammal is selected from the group consisting of pigs, sheep, horses, cattle, cats and dogs.

In a particular embodiment, the non-human mammal is a pig.

In a particular embodiment, the non-human mammal is a dog.

In a particular embodiment, the non-human mammal is a cat.

In a particular embodiment, the non-human mammal is a cow.

In an eighteenth embodiment, the invention concerns a device for administering to a non-human mammal a composition according to one of embodiments 6 to 10 or a formulation according to one of embodiments 11 to 13, comprising a means for diffusing said composition or said formulation so as to allow said composition or said formulation to be diffused for a period of 1 to 35 days.

In a nineteenth embodiment of the present invention is also provided a device according to the eighteenth embodiment, characterized in that it is selected from the group consisting of a vaporizer containing said composition or said formulation, an electric diffuser fitted with a wick and containing said composition or said formulation, an accessory designed to be carried by the non-human mammal and impregnated with said composition or said formulation.

Lastly, the present invention is directed in a twentieth embodiment at a kit comprising a composition according to one of embodiments 6 to 10, a formulation according to one of embodiments 11 to 13 and/or a device according to embodiment 18 or 19, and a set of instructions, for decreasing stress, aggressiveness and/or anxiety of a non-human mammal.

In a particular embodiment, the non-human mammal is a pig.

In a particular embodiment, the non-human mammal is a dog.

In a particular embodiment, the non-human mammal is a cat.

In a particular embodiment, the non-human mammal is a cow.

In the context of the present invention, the alkyl group R refers to a linear aliphatic chain comprising 2 to 30 carbon atoms, particularly 10 to 30 carbon atoms, even more particularly 12 to 25 carbon atoms. This term "alkyl" includes saturated or unsaturated aliphatic chains, particularly monounsaturated and diunsaturated. The preferred saturated chains include C8, C10, C12, C14, C16, C18 or C20 chains, for example. The unsaturated chains include C16:1, C18:1 or C22:1 chains, for example.

As mentioned, the fatty acid derivatives according to the invention may comprise fatty acid esters, i.e., a fatty acid whose carboxylic acid function is engaged with an alcohol function to form an ester bond, i.e., the result of esterification of the carboxyl group (—COOH) of a fatty acid with a hydroxylated compound. The fatty acid esters according to the invention may be selected from the esters of fatty acids with alcohols such as methanol, ethanol, propanol or butanol, for example.

The fatty acid derivatives according to the present invention may also include fatty acid thioesters, i.e., a fatty acid whose carboxylic acid function is engaged with the thiol function to form a thioester bond.

The fatty acid derivatives according to the invention may also include fatty acid amides, which are fatty acids whose carboxyl group (—COOH) has been substituted by an amide group (—CONH$_2$).

Furthermore, as described above, most soothing compositions for mammals comprise molecules present in mother's milk or secreted by the mammary glands: fatty acids, 2-methyl-2-butenal, etc. Another type of molecule is present in breast milk: glycerol ethers, more commonly called alkyl glycerol (AKG), found in shark liver oil. These compounds are used in traditional medicine in the Nordic countries. They are known for their capacity to improve immune defenses. Mother's milk, notably human breast milk, cow's milk and ewe's milk, for example, contains many AKGs. Expressed as a percentage, the most important are C16:0 AKG, C18:0 AKG and C18:1 AKG. Human milk also contains other AKGs in notable amounts, namely AKG C22:1 and AKG C24:1. AKG distributions are thus species-dependent, which makes this family specific to each species.

To form the compound (1) concerned by the present invention, the Applicant was thus particularly interested in the radicals R, such as, when 2-methyl-2-butenal is released in the presence of an acid catalyst, the molecule thus formed by cleavage is also of interest for the application of the present invention, i.e., the soothing of non-human mammals. This second molecule may for example be one of the AKGs corresponding to those present in mother's milk as mentioned above, for example, or one of the glycerol fatty esters (monoglycerides), which also are present in milk, for example.

In an embodiment of the present invention is also provided a method for preparing a compound (1) according to the present invention, in particular according to one of embodiments 1 to 3, according to Scheme 1, by reacting an AKG or a monoglyceride comprising a radical R, with 2-methyl-2-butenal, in anhydrous medium with a pyridinium followed by a base wash as indicated below.

Scheme 1

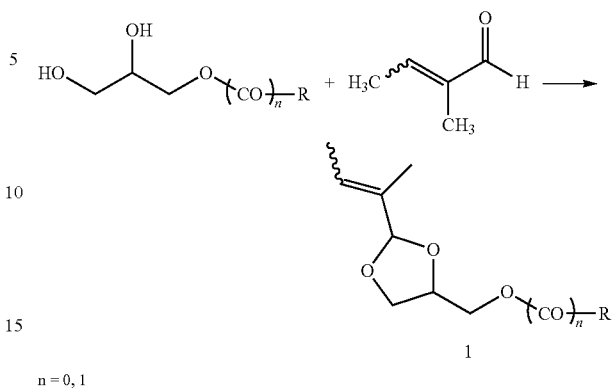

n = 0, 1

Wherein n is equal to 0 or 1 and R represents a saturated or unsaturated linear alkyl group having 2 to 30 carbon atoms.

In an embodiment, n=0 and R is a saturated or unsaturated linear alkyl group having 9 to 30 carbon atoms, more particularly 12 to 30 carbon atoms.

In another embodiment, n=1 and R is a saturated or unsaturated linear alkyl group having 2 to 30 carbon atoms, more particularly 8 to 22 carbon atoms.

Compositions According to the Invention

The active compositions according to the invention are pro-pheromonal compositions based on novel compounds of the general formula (1) and fatty acids or derivatives thereof. The term "pro-pheromonal" means that the composition releases molecules known for their pheromonal action.

The compositions according to the invention consist of a mixture of a compound (1), which makes up between 0.1% and 5% by weight of the total composition, preferably 1% by weight, and one or more fatty acids having a number of carbon atoms between 6 and 30, or derivatives thereof, which make up at least 85% by weight, indeed 90% by weight, preferably between 99.5% and 90% by weight, of the composition.

As mentioned, the present invention concerns a veterinary composition comprising a compound (1) according to the present invention and at least one fatty acid or fatty acid derivative. The presence of at least one fatty acid in a composition according to the invention makes it possible to catalyze the slow decomposition of the compound (1) to 2-methyl-2-butenal and to AKG or monoglyceride having the radical R.

The compositions and formulations according to the invention take into account the high volatility of 2-methyl-2-butenal (boiling point <100° C.) and the low volatility of the fatty acids (boiling point >180-200° C.). Indeed, the low acidity and the pKa near 5 of the fatty acids allow slow hydrolysis of the compound (1), which will thus release 2-methyl-2-butenal. This aldehyde will then quickly evaporate due to the high volatility and the equilibrium of the chemical equation of Scheme 1 will shift toward its increased formation, which has as a consequence controlled release of 2-methyl-2-butenal. The implementation of high temperature facilitates the evaporation of 2-methyl-2-butenal, which accelerates the hydrolysis reaction by shifting the equilibrium. This is what happens when a composition or a formulation according to the invention is contacted with a diffusion device heating at temperatures on the order of 70°

C. to 110° C., such as flasks fitted with a porous wick in contact with a heating body or when cellulose pads impregnated with a composition or formulation according to the invention are contacted with the heating element of electric diffusers. In an alternative mode of diffusion, a formulation according to the invention may be vaporized into the air or onto a support. Under these conditions, the solvent quickly evaporates and, as a result, the compound (1) and fatty acid mixture is concentrated. Consequently, the 2-methyl-2-butenal, whose release is initiated via hydrolysis of the compound (1) via the presence of the fatty acid, will easily evaporate due to the large contact surface area, which will unbalance the equilibrium reaction toward generation of 2-methyl-2-butenal. The fatty acids, although less volatile, will despite all be detected by the animal. In a situation in which the diffusion system is a device impregnated with the composition or formulation according to the invention, such as for example a collar or an earring, it is the animal's body heat that makes it possible to reach temperatures on the order of 40° C. at said device, which will initiate diffusion of the 2-methyl-2-butenal and trigger controlled release of this compound and the fatty acids.

When a composition, formulation or device according to the invention is packed in a closed container, a small portion of 2-methyl-2-butenal is generated by acid hydrolysis but, due to the absence of evaporation of said 2-methyl-2-butenal, the reaction equilibrium is maintained and the compound (1) decomposes not at all or only at a negligible rate over the shelf life of said device.

By the expression "fatty acid derivative" is meant herein a fatty acid ester, a fatty acid thioester or a fatty acid amide as defined above.

The composition according to the invention may thus comprise at least one fatty acid selected from the group consisting of lauric acid, linoleic acid, linolenic acid, palmitic acid, pentadecanoic acid, capric acid, oleic acid, myristic acid, palmitoleic acid, azelaic acid, pimelic acid and mixtures thereof.

The invention also relates to the use of the veterinary compositions according to the invention, which may be pure or diluted in solvent or diffusing material, to soothe mammals such as ungulates (pigs, cattle, goats, sheep), horses, dogs, cats. Preferably, the diluted active formulations will be diffused by means of vaporizers, thermal diffusers or collars.

The present invention thus concerns a formulation containing a composition according to the invention and a solvent.

The solvent of a formulation according to the invention may be selected from the group consisting of water, alcohols, glycols, polyglycols, paraffin and mixtures thereof. The solvent may be particularly isopropanol, ethanol, a water/ethanol mixture, paraffin, isoparaffin, dipropylene glycol methyl ether, propylene glycol propyl ether or tripropylene glycol methyl ether, or mixtures thereof, for example.

The amount of solvent in a formulation according to the invention may be between 80% and 99.5% by weight of the formulation, more particularly between 85% and 99% by weight of the formulation, even more particularly between 90% and 99% by weight of the formulation.

The invention also relates to the use of such formulations to improve the yield of pig, sheep, goat or cattle farms.

A formulation according to the invention may comprise a composition according to the present invention in amounts on the order of 0.5% to 20% by weight of the formulation, particularly 1% to 15% by weight of the formulation, even more particularly 1% to 10% by weight of the formulation.

The compositions and formulations according to the invention can be diffused into the ambient air using all means or devices for vaporizing, spraying, nebulizing or generating aerosols or for diffusing by kinetic heating as described above. The devices, whether heating or not, able to diffuse into the ambient air the fatty acids and 2-methyl-2-butenal according to the invention, may comprise, by way of example, aerosols, pneumatic or ultrasonic nebulizers, ultrasonic sprayers, or by combustion heat sources such as a candle flame, a benzene burner, a gas stove, slow-burning wood, or a piezoelectric sprayer or a contact heat source, such as electrical resistance, a water or oil bath, or a solar heat source, such as an optical device that concentrates light rays. Preferably, the selected heat source makes it possible to reach a temperature between 70° C. and 120° C. for 1 to 35 days.

At room temperature, the compositions and formulations according to the invention may be in liquid form or in solid form, as a function of the length and the structure of the carbon chain R and that of the fatty acids but also as a function of the solvent.

When the compositions or formulations according to the invention are in liquid form, they may be diffused via a vaporizer in order to deposit an adequate amount at a precise and given point, such as the basket or the litter of the non-human mammal which it is desirable to soothe. The solvent will then quickly evaporate and leave remaining the compound (1) and fatty acid or fatty acid derivative mixture. The evaporation of the 2-methyl-2-butenal will modify the reaction equilibrium and its release will occur in a slow and controlled manner.

When the compositions or formulations are in solid form, they may be placed near a heat source as described above. When the compositions or formulations according to the invention are in a liquid oil phase, they are absorbed onto a diffusion means, such as a porous support that is heated in order to diffuse the mixtures described above. These porous supports may be selected as a function of their chemical nature so that there is no chemical interaction, particularly no degradation of the fatty acids of the compositions or formulations described above. By way of examples of porous supports that are capable of absorbing an effective amount of a composition or formulation according to the present invention, mention may be made of natural or synthetic polymeric matrices, for example composed of PVC or latex; crystalline or amorphous mineral matrices, made up for example of ceramics or pumice stone; organic matrices, for example of wood, of plant fibers such as cotton or bamboo fibers.

The porous supports may be enclosed within a hermetic jacket, before their implementation, having an opening for controlling the kinetics of diffusion. The jacket may be selected for its chemical compatibility with the fatty acids in contact with the internal film, its water tightness and its capacity to conduct heat homogeneously. By way of example, the material of which the jacket consists may be a plastic comprised of several layers of different kinds of polymers, or a metal film, for example an aluminum film, or superimposed layers of different kinds of films, for example of plastic, of organic films, or of metal films. In the context of a composition or formulation in the liquid state, it may be preserved and stored in a sealed flask.

In a specific case, the porous or non-porous support may be an accessory carried by the mammal, in particular a collar, an earring, for example, made of plastic material impregnated with a composition or formulation according to the invention in an amount allowing its diffusion according to the kinetics mentioned above, and this thanks to the body heat of the animal carrying said accessory.

The compositions and formulations according to the invention are particularly suitable for treating anxiety, stress or aggressiveness in cats, dogs, pigs or cows.

EXAMPLES

Example 1: Synthesis of a Compound According to the Invention Wherein R is $C_{22}H_{43}$ with n=0

Into a 250 mL three-neck round-bottom flask under nitrogen atmosphere is introduced cis-13-docosenol (15.0 g; 46.21 mmol) and triethylamine (9.6 mL; 69 mmol) dissolved in 50 mL of methyltetrahydrofuran. The reaction medium is cooled to 0° C. then mesyl chloride (3.9 mL; 50.80 mmol) in solution in 25 mL of methyltetrahydrofuran. The reaction medium is then allowed to return to room temperature and is stirred for 90 minutes. 100 mL of water is then introduced. The organic phase is then washed with 100 mL of aqueous HCl solution (0.1 N), 100 mL of water (emulsion), 100 mL of brine solution, dried over $MgSO_4$, filtered and concentrated under vacuum. A colorless oil that crystallizes at room temperature is then obtained (16.1 g; 86%). The crude reaction product is used as such in the following condensation step with solketal (see $^1$H NMR).

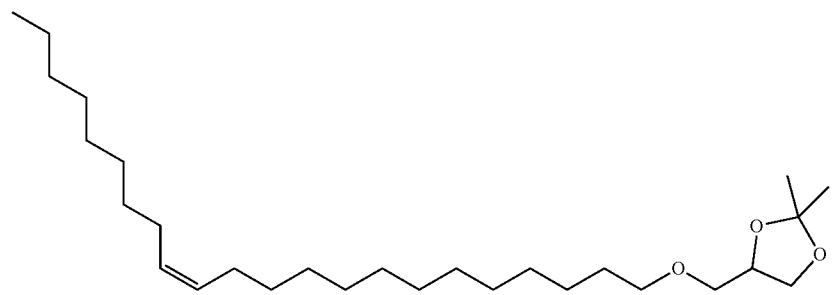 [SMILES: CCCCCCCC/C=C\CCCCCCCCCCCCOCC1COC(C)(C)O1]

Into a 500 mL three-neck round-bottom flask fitted with a Dean-Stark apparatus and under nitrogen atmosphere is introduced finely ground KOH suspended in toluene (110 mL). Solketal (4.3 mL; 34.7 mmol) and the mesylate derivative synthesized beforehand (15.9 g; 39.50 mmol) are introduced. The medium is then heated at reflux for 16 hours. The reaction is then quenched by addition of 200 mL of water then 100 mL of ethyl acetate is added so as to have two clear phases. The cloudy aqueous phase is then extracted again with 2×100 mL of ethyl acetate, washed with brine (100 mL), dried over $MgSO_4$, filtered and concentrated under vacuum to lead to the expected product in the form of an orange oil (16.0 g; 93%).

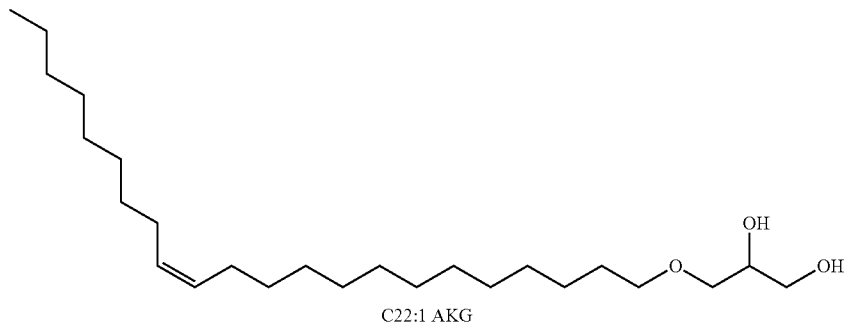 [SMILES: CCCCCCCC/C=C\CCCCCCCCCCCCOCC(O)CO]

C22:1 AKG

In a 500 mL single-neck round-bottom flask under nitrogen atmosphere, the dioxolane derivative (15.80 g; 36.0 mmol) is dissolved in a methanol/$H_2O$ mixture (158/15 mL). APTS (300 mg; 1.74 mmol) is then added to the reaction medium, which is heated at reflux for 3 hours. The medium is cooled then the methanol is evaporated under vacuum. The residue is then taken up in 100 mL of ethyl acetate, washed with saturated aqueous $NaHCO_3$ solution, 100 mL of water, and brine (100 mL), dried over $MgSO_4$, filtered and concentrated under vacuum to lead to an oil that crystallizes at room temperature. The product is crystallized in hexane (50 mL) to lead to a white solid (9.0 g; 63%).

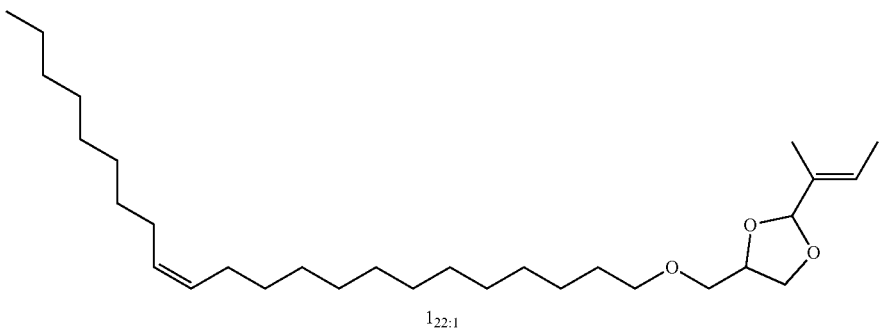

compound (1)

Into a 50 mL three-neck round-bottom flask under nitrogen atmosphere is introduced the C22:1 alkylglycerol derivative (7 g; 17.00 mmol) and pyridinium para-toluenesulfonate (43 mg; 0.17 mmol) in solution in toluene (90 mL). Tiglic aldehyde (11.5 mL; 0118 mmol) in solution in 10 mL of toluene is added to the reaction medium, which is then heated at reflux for 3 hours. The reaction medium is neutralized by addition of saturated $NaHCO_3$ solution (50 mL). After decanting, the aqueous phase is extracted with ethyl acetate (50 mL).

The organic phases are then combined, washed with brine solution, dried over $MgSO_4$, filtered and concentrated under vacuum to lead to a light-yellow oil (8.0 g). This oil is then purified by flash chromatography to lead to a colorless oil (6.0; 74%).

The table below presents the different alkylglycerols synthesized and sampled, as well as the operating conditions and the overall yields. The procedures used for the synthesis of C22:1 AKG appear in the experimental section.

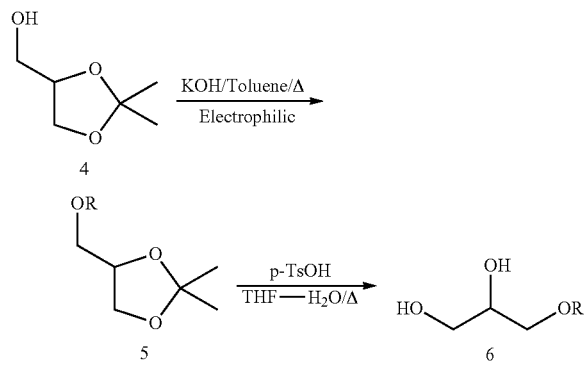

| R | AKG | Conditions | Electrophile leaving group | Product 1 formed | Yield (% mol.) |
|---|---|---|---|---|---|
| $C_8H_{17}$ | $C_{8:0}$ | A | Iodine | $1_8$ | 37 |
| $C_{10}H_{21}$ | $C_{10:0}$ | B | Bromine | $1_{10}$ | 68 |
| $C_{12}H_{25}$ | $C_{12:0}$ | B | Bromine | $1_{12}$ | 62 |
| $C_{14}H_{29}$ | $C_{14:0}$ | B | Bromine | $1_{14}$ | 65 |
| $C_{16}H_{33}$ | $C_{16:0}$ | B | Mesylate | $1_{16}$ | 66 |
| $C_{16}H_{31}$ | $C_{16:1}$ | C | Mesylate | $1_{16:1}$ | 66 |
| $C_{18}H_{37}$ | $C_{18:0}$ | B | Mesylate | $1_{18}$ | 65 |
| $C_{18}H_{35}$ | $C_{18:1}$ | C | Mesylate | $1_{18:1}$ | 66 |
| $C_{18}H_{35}$ | $C_{18:2}$ | C | Mesylate | $1_{18:2}$ | 64 |
| $C_{20}H_{41}$ | $C_{20:0}$ | B | Bromine | $1_{20}$ | 71 |
| $C_{22}H_{43}$ | $C_{22:1}$ | C | Mesylate | $1_{22:1}$ | 50 |

Conditions A: 1) Solketal/KOH/RI/DMSO/50° C. 2) APTS/MeOH/$H_2O$.

Conditions B: 1) Solketal/KOH/RBr/Toluene/DS/2) APTS/MeOH/$H_2O$.

Conditions C: 1) $CH_2Cl_2$/$Et_3N$/MsCl 2) Solketal/KOH/ROMs/Toluene/DS/Δ3) APTS/MeOH/$H_2O$.

GC Method Used:

Equipment: GC, Hewlett Packard 5890 Series II

Detector FID

Column: HP5 30 m, 0.53 mm, 0.88 μm

Pressure: 11 psi

Injection volume: 1 μL

Sample preparation: 4 mg/mL in AcOEt

Injector temperature: 270° C.

Detector temperature: 280° C.

Oven:

| | |
|---|---|
| Initial temperature | 170° C. |
| Initial time | 3 min |
| Gradient | 5° C./min |
| Final temperature | 260° C. |
| Final time | 10 min |
| Run | 31 min |

Example 2: Preparation of Soothing Active Formulations

The soothing formulations are prepared in a precise order since the principle of the invention consists in combining a compound (1) with a fatty acid catalyst of its degradation. The method thus consists in introducing into a stirred-reactor type mixer the formulation solvent, the fatty acid or the mixture of fatty acids. Stirring is maintained for 1 hour, after which the medium is perfectly homogeneous, then the compound (1) is added and stirring is maintained for another hour.

The following table lists the mixtures that were prepared

| Example | Solvent (v/v) | Amount of solvent (g) | Fatty acids | Amount of fatty acid (g) | Compound (1) | Amount of compound (1) (g) |
|---|---|---|---|---|---|---|
| 2a | Ethanol/water 90/10 | 85 | Linoleic/Pentadecanoic 95:5 | 12 | $1_{18}$ | 3 |
| 2b | Isopropanol | 85 | Linoleic/Pentadecanoic 95:5 | 12 | $1_{18}$ | 3 |
| 2c | Isopar V paraffin | 90 | Linoleic | 9.7 | $1_{22:1}$ | 0.3 |
| 2d | Isopar V paraffin | 95 | Linoleic | 4.85 | $1_{22:1}$ | 0.15 |
| 2e | Isopar V paraffin | 98 | Linoleic | 1.94 | $1_{22:1}$ | 0.06 |
| 2f | Dipropylene glycol methyl ether | 99 | Linoleic | 0.9 | $1_{22:1}$ | 0.09 |
| 2g | Propylene glycol propyl ether | 99 | Linoleic | 0.9 | $1_{22:1}$ | 0.09 |
| 2h | Propylene glycol methyl ether | 99 | Linoleic | 0.9 | $1_{22:1}$ | 0.09 |

Example 3: In Vitro Study of 2M2B Release

The solution prepared in Example 2b is used in a climatic chamber at 100° C. and 30° C. (conditions corresponding either to the temperature of a thermal diffuser or to room temperature). Samples are taken at regular intervals and the disappearance of compound $1_{22:1}$ and the appearance of $C_{22:1}$ AKG is measured by gas chromatography. The results are presented in the following table (the percentages are expressed only taking into consideration integration relative to compound $1_{18}$ and of $C_{18:0}$ AKG):

| T = 100° C. | 0 | 3 h | 6 h | 1 d | 2 d | 7 d | 14 d | 21 d | 28 d |
|---|---|---|---|---|---|---|---|---|---|
| % $1_{18}$ | 100 | 52 | 25 | 2 | 0 | 0 | 0 | 0 | 0 |
| % $C_{18:0}$ | 0 | 48 | 75 | 98 | 100 | 100 | 100 | 100 | 100 |

-continued

| AKG | | | | | | | | | |
|---|---|---|---|---|---|---|---|---|---|
| T = 30° C. | 0 | 3 h | 8 h | 1 d | 2 d | 7 d | 14 d | 21 d | 28 d |
| % $1_{18}$ | 100 | | 100 | 100 | 100 | 99.5 | 99 | 99 | |
| % $C_{18:0}$ AKG | 0 | | 0 | 0 | 0 | 0.5 | 1 | 1 | |

This table shows that degradation of the product $1_{18}$ is well stimulated by high temperature (electric diffuser-type) but that in its diluted state at room temperature the solution is sufficiently stable to provide the treatment for one month (less than 5% loss over the period).

Likewise, we noted that the solutions of Examples 2f, 2 g and 2h have similar trans-2-methyl-2-butenal release kinetics and this despite a different kind of dilution solvent.

Example 4: Formulation for Thermal Diffuser and Release Curve 50 mL of the formulations prepared in Examples 2c, 2d and 2e are used to fill three PET flasks fitted with a diffusion wick. Each flask is screwed onto an electric diffuser characterized in that the ceramic of which it is composed is heated to about 100° C. when the system is connected up.

The daily release of the formulation is then measured and the results are presented in the following table: Evaluated is the total loss of weight of the formulation reflecting the release of 2-methyl-2-butenal, the fatty acid and the combined solvent.

| | Days | | | | | | | | | | | | |
|---|---|---|---|---|---|---|---|---|---|---|---|---|---|
| Formula | 1 | 2 | 3 | 4 | 5 | 6 | 7 | 14 | 21 | 28 | 35 | 42 | 49 | 56 |
| 2c | 1 | 0.5 | 0.3 | 0.3 | 0.2 | 0.2 | 0.1 | 0.1 | 0.05 | 0.05 | — | — | — | — |
| 2d | 0.9 | 1 | 0.8 | 0.6 | 0.4 | 0.2 | 0.2 | 0.15 | 0.15 | 0.15 | 0.15 | 0.15 | 0.15 | 0.15 |
| 2e | 0.9 | 1.2 | 1.2 | 1.2 | 0.7 | 0.8 | 0.7 | 0.4 | 0.4 | 0.3 | 0.3 | 0.3 | 0.3 | 0.3 |

The table expresses the daily diffusion in grams of each formulation

At day 35, the residual compositions in each flask are measured by liquid chromatography and compared with the initial compositions.

| Formula | Initial composition | Composition after 35 d of diffusion |
|---|---|---|
| 2c | 90/9.7/0.3 | 88/11.6/0.1 |
| 2d | 95/4.85/0.15 | 95/4.95/0.15 |
| 2e | 98/1.94/0.06 | 98/1.94/0.06 |

The table expresses the content of each solution according to the ratio paraffin/linoleic acid/$1_{22:1}$ Based on the preceding measurements, we can estimate that the amounts released over the 35-day period by molecules going into each composition are the following (in grams):

| Formula | 2c | 2d | 2e |
|---|---|---|---|
| Linoleic acid | 0.195 | 0.188 | 0.2 |
| $1_{22:1}$ | 0.05 | 0.0063 | 0.0063 |

These results show that the product $1_{22:1}$ and linoleic acid disappear from the formulation at flow rates that respect the orders of magnitude defined in the formulation.

By considering that at 100° C., all of product $1_{22:1}$ decomposes as was shown in Example 3, we can estimate the daily amounts of the various products released into the atmosphere according to the various formulae.

2% Formula (2e)

| Product | Daily amount (mg) |
|---|---|
| Linoleic acid | 5.8 |
| $C_{22:1}$ AKG | 0.14 |
| 2-Methyl-2-butenal | 0.036 |

5% Formula (2d)

| Product | Daily amount (g) |
|---|---|
| Linoleic acid | 5.1 |
| $C_{22:1}$ AKG | 0.14 |
| 2-Methyl-2-butenal | 0.036 |

10% Formula (2c)

| Product | Daily amount (mg) |
|---|---|
| Linoleic acid | 5.5 |
| $C_{22:1}$ AKG | 1.2 |
| 2-Methyl-2-butenal | 0.32 |

Example 6: Study of the Soothing Effect on Pigs

The tests were carried out with electric diffusers like those described in Example 5.

The protocol is as follows:

One hundred 3-week-old piglets are distributed among 4 pigsties on 25 m² grating (or 175 m³). The piglets are divided into populations of 25 called A, B, C, D. Population A is treated with a diffuser containing only Isopar V paraffin.

Population B is treated by a diffuser containing the formula of Example 2e (2%).

Population B is treated by a diffuser containing the formula of Example 2d (5%).

Population B is treated by a diffuser containing the formula of Example 2c (10%).

The tests are conducted for 28 days. The average weight of each population and the average number of visible wounds are measured each week.

The results are presented in the following tables:

| Weight change as a function of piglet age (kg) | A | B | C | D |
|---|---|---|---|---|
| Weight at 21 days | 6.513 | 6.513 | 6.513 | 6.513 |
| Weight at 28 days | 7.081 | 7.075 | 7.078 | 7.051 |
| Weight at 35 days | 9.153 | 9.161 | 9.175 | 9.169 |
| Weight at 42 days | 11.815 | 12.012 | 12.02 | 12.07 |
| Weight at 49 days | 14.989 | 15.206 | 15.281 | 15.601 |

| Daily average weight gains (kg) | A | B | C | D |
|---|---|---|---|---|
| Week 1 | 0.08 | 0.08 | 0.08 | 0.08 |
| Week 2 | 0.30 | 0.30 | 0.30 | 0.30 |
| Week 3 | 0.38 | 0.41 | 0.41 | 0.41 |
| Week 4 | 0.45 | 0.46 | 0.47 | 0.50 |

The number of bites over the four weeks of treatment is 10% to 12% lower for populations B, C and D compared with population A.

Example 7: Soothing Effect on Kittens

A 60 mL vaporizer is filled with the formulation of Example 2a. Another vaporizer containing a methanol/water mixture (90:10 v/v) is used as a placebo.

Six 1-month-old kittens from the same litter are separated from their mother and divided into two groups of three (2 males and 1 female in each group). Group A is placed in a basket onto which formulation 2a is vaporized every 12 hours. Group B is placed in a basket vaporized every 12 hours with the placebo.

In the first week, the population A kittens are calm and sleep against one another 16 hours per day on average whereas the population B kittens sleep at most 14 hours and at the end of the third day regularly fight.

The behaviors of the two populations converge the second week.

This example shows that formulation A by vaporizer improves the kittens' adaptation to weaning.

The invention claimed is:

1. A compound of the general formula (1):

n = 0, 1 wherein n=0 and R is a saturated or unsaturated linear alkyl group having 9 to 30 carbon atoms, or n=1 and R is a saturated or unsaturated linear alkyl group having 8 to 22 carbon atoms.

2. A method for treating anxiety, stress or aggressiveness in a nonhuman mammal comprising the administration of a veterinary medicinal product comprising the compound according to claim 1 to the non-human mammal.

3. The method according to claim 2, wherein the non-human mammal is selected from the group consisting of pigs, sheep, horses, cattle, cats and dogs.

4. A veterinary composition comprising a compound according to claim 1 and at least one fatty acid for an ester of the fatty acid wherein the ester comprises alcohols selected from the group consisting of: methanol, ethanol, propanol, and butanol.

5. The composition as claimed in claim 4, wherein the acid is a fatty acid having 6 to 30 carbon atoms.

6. The composition as claimed in claim 5, wherein the fatty acid is selected from the group consisting of lauric acid, linoleic acid, linolenic acid, palmitic acid, pentadecanoic acid, capric acid, oleic acid, myristic acid, palmitoleic acid, azelaic acid, pimelic acid and mixtures thereof.

7. The composition as claimed in claim 4, wherein the amount of the compound is between 0.1% and 5% by weight of the composition.

8. The composition as claimed in claim 4, wherein the amount of fatty acid or ester of the fatty ester is between 95% and 99.9% by weight of the composition.

9. A formulation comprising the composition as claimed in claim 4 and a solvent.

10. The formulation as claimed in claim 9, wherein the solvent is selected from the group consisting of water, alcohols, glycols, polyglycols, paraffin and mixtures thereof.

11. The formulation as claimed in claim 9, wherein the solvent is selected from the group consisting of water, ethanol, isopropanol, paraffin, dipropylene glycol methyl ether, propylene glycol propyl ether, tripropylene glycol methyl ether and mixtures thereof.

12. A kit comprising the composition as claimed in claim 4, and a device for administering to a non-human mammal the composition as claimed in claim 4 wherein the device is selected from the group consisting of: a vaporizer containing said composition, an electric diffuser fitted with a wick and containing said composition, an accessory designed to be carried by the non-human mammal and impregnated with said composition, for decreasing stress, aggressiveness and/or anxiety in a non-human mammal.

* * * * *